United States Patent [19]

Gagnebin

[11] Patent Number: 5,235,324
[45] Date of Patent: Aug. 10, 1993

[54] DETECTOR FOR OVER-PRESSURE INSIDE A PIPE AND A PUMP FITTED WITH SUCH A DETECTOR

[75] Inventor: Eric Gagnebin, Marin, Switzerland
[73] Assignee: Asulab S.A., Bienne, Switzerland
[21] Appl. No.: 724,780
[22] Filed: Jul. 2, 1991
[30] Foreign Application Priority Data
  Jul. 23, 1990 [FR] France .............................. 90 09477
[51] Int. Cl.⁵ .............................................. G08B 21/00
[52] U.S. Cl. ...................................... 340/626; 340/603;
  200/81 R; 200/82 R; 137/557
[58] Field of Search ........................ 340/626, 603, 451;
  73/700, 744, 745, 756, 146.2; 137/551, 553, 554,
  557; 200/81 R, 81.5, 82 R

[56] References Cited

U.S. PATENT DOCUMENTS 3,939,316  2/1976  Stropkay ..................... 340/626 X
4,363,020  12/1982  Venena ..................... 73/146.5 X

FOREIGN PATENT DOCUMENTS 3035703  5/1982  Fed. Rep. of Germany .

OTHER PUBLICATIONS

International Publication No. WO 86/07266 corresponding to International Application No. PCT/GB86/00318 filed Jun. 5, 1986.

Primary Examiner—Jin F. Ng
Assistant Examiner—Jeffery A. Hofsass
Attorney, Agent, or Firm—Pollock, Vande Sande & Priddy

[57] ABSTRACT

The invention concerns a simple, inexpensive and small detector, particularly for use in the medical pumps, for detecting over-pressure in a pipe (1) and setting off an alarm when an over-pressure is detected. The detector for detecting over-pressure in the pipe (1) along which a fluid (3) flows may comprise a T junction (5) for deriving a fraction of the flowing fluid (3) from the pipe (1); at least one tube (7) wherein there is fitted at least one obturating member (9); and an assembly for detecting the displacement of the obturating member (9) in the tube (7) and for generating a signal in response to detecting displacement of the obturating member (9).

20 Claims, 5 Drawing Sheets

DETECTOR FOR OVER-PRESSURE INSIDE A PIPE AND A PUMP FITTED WITH SUCH A DETECTOR

BACKGROUND OF THE INVENTION

The present invention concerns a detector for over-pressure inside a pipe and a pump fitted with such a detector. Although the application of this detector is not limited to any particular type of pipe, it is particularly suited for use with small diameter pipes.

In fluid supply systems comprising a pump for moving a liquid or gas inside a tube, the pipe may become partly or completely blocked causing an over-pressure therein. In many instances, it is imperative to detect such over-pressure and stop the pump as quickly as possible in order to avoid deformation or even rupture of the pipe and to ensure that the pump should not continue to operate unwantedly.

It will readily be understood that such problems are particularly serious for medical pumps, for example a peristaltic pump such as that described in French patent application FR-9 003 869 which is owned by the assignee of the present application. This medical pump is designed to pump liquid medication along a pipe connecting a reservoir to a hypodermic injection needle. If this pipe becomes blocked, there is a risk that the medication is no longer delivered to the patient, which can disturb the treatment and cause discomfort to or even be dangerous for the patient. Moreover, the pump may be damaged.

It is therefore necessary to provide a detector which sets off an alarm or even interrupts operation of the pump as soon as the over-pressure in the pipe exceeds a given threshold.

Furthermore, to the extent that medical pumps are often intended for one-time use in a single application, and are discarded after having been used for a given number of days, it would also be desirable to have a detector also for one-time use The provision of a detector for one-time use implies of course that its cost price should be as low as possible.

Lastly, this detector should be of sufficiently small size for it, for example, to be integrated directly into the pump.

Detectors are known in which a piston or a valve member is moved relative to its seat by a fluid against the action of an elastic member in the case of an over-pressure, with the piston or the valve member being connected to means for detecting its deplacement. It has also been proposed to use in pressure detection systems the principle of the Bourdon tube as used in conventional pressure gauges and pressure controllers, and quartz sensors or strain gauges. These devices are however quite large, expensive and are not necessarily suited for medical use.

SUMMARY OF THE INVENTION

The invention therefore aims to remedy these drawbacks.

To this end, the invention proposes a detector, preferably for single use, for over-pressure in a pipe in which a fluid flows, this detector being adapted to produce a signal when an over-pressure threshold is reached.

According to the invention, this detector comprises:
means for deriving a fraction of the flowing fluid from the pipe,
at least one tube wherein there is fitted at least one obturating member, this tube being connected at its upstream end to said deriving means, one of the elements making up the tube and the obturating member being resiliently deformable whereby the obturating member is retained in the tube in a normal operating position by means of frictional forces generated at their contacting surfaces, the obturating member leaving the normal operating position when the tube is subjected to an over-pressure sufficient to overcome the frictional forces, and
means for detecting the displacement of the obturating member and for generating said signal in response to detecting displacement of the obturating member.

By means of these features of the invention, an over-pressure or exceeding an over-pressure threshold in the pipe is detected easily, because this over-pressure immediately acts in the detector tube. During normal operation, the fluid pressure in the tube upstream of the obturating member is balanced by the air pressure downstream of this obturating member and by the frictional forces exerted by the obturator member on the tube. However, if there is an over-pressure, the pressure exerted by the fluid is greater than that of the air and the frictional forces. Above a certain over-pressure, the obturating member moves downstream inside the tube towards the displacement detecting means.

This detector is made up of only a few parts and is thus inexpensive to produce.

BRIEF DESCRIPTION OF THE DRAWINGS

The invention will be better understood from the following description given solely by way of example and with reference to the accompanying drawings, in which.

DETAILED DESCRIPTION

Figure 1A:
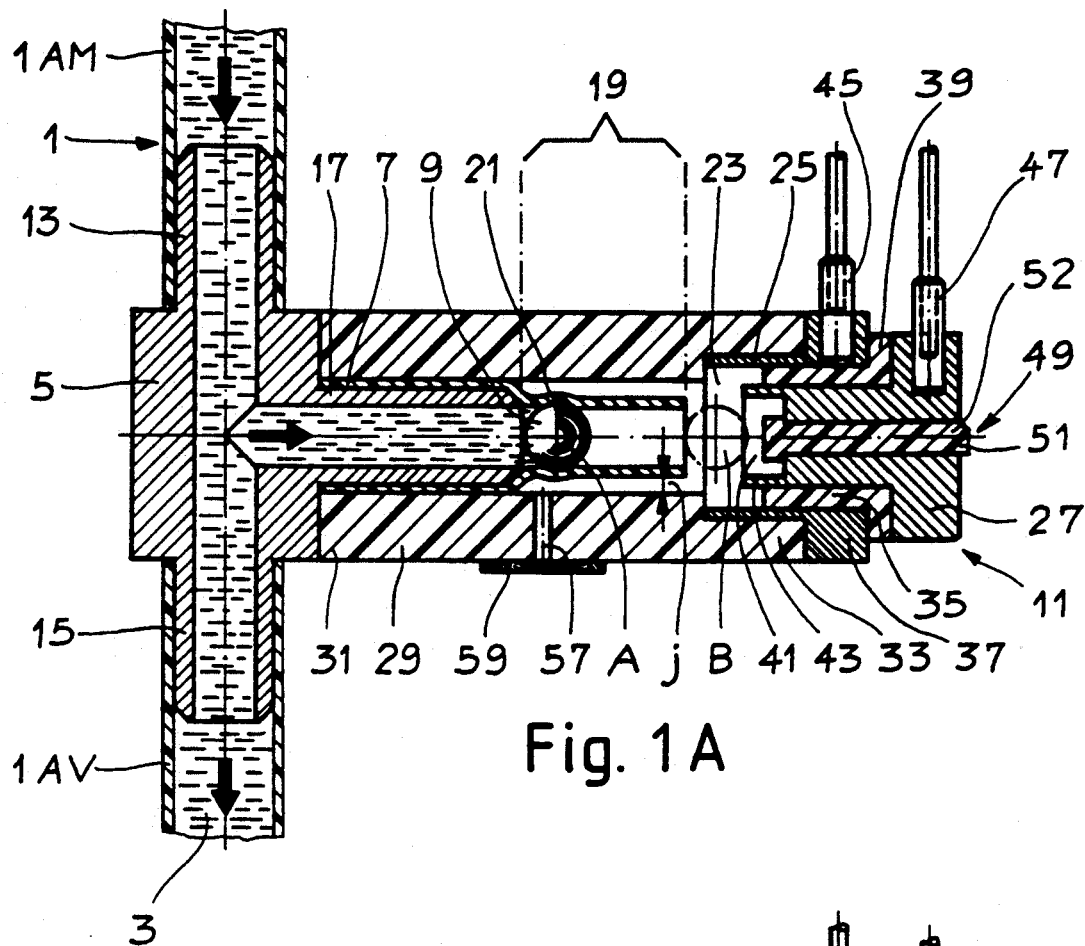
FIGS. 1A and 2A are cross-sectional views of first and second embodiments of the detector according to the invention.

A first embodiment of the detector according to the invention is shown in FIG. 1A. This detector is designed firstly to detect an over-pressure, or when an over-pressure threshold is exceeded, in a pipe 1 through which a fluid 3 flows, and secondly to generate a signal as soon as this threshold is reached. The signal generated is usually an electrical signal.

In this embodiment, the fluid 3 is necessarily a conductive liquid.

The detector comprises means 5 for deriving a fraction of liquid 3 from the pipe 1, a tube 7 in which is friction-fitted an obturator 9 and means 11 for detecting displacement of the obturator 9.

The deriving means 5 are made of a T junction, for example of low-cost plastic material. Junction 5 has an inlet branch 13 coaxial with an outlet branch 15, as well as a third, derivation branch 17 perpendicular to the two others. In the following description, the terms upstream and downstream are defined relative to the direction of flow of fluid 3. The pipe 1, for example made of silicone, is cut into two parts. The upstream part 1AM, connected to the pump (not shown) circulating liquid 3, is fitted on the inlet branch 13. The downstream part 1 AV, leading towards the fluid outlet, is fitted on the outlet branch 15. The upstream part of tube 7 is fitted on the derivation branch 17.

Preferably, tube 7 is made of resiliently deformable material, for example of silicone. Its length is sufficient to entirely cover the branch 17 so that it is fixed firmly thereon, while leaving a free downstream portion 19 in which the obturator 9 can move.

The obturator 9 is preferably a ball as shown in FIG. 1, but it could also take the form of a rotation-symmetric body, or body of revolution, such as a cylinder for example. The diameter of ball 9 is slightly greater than the internal diameter of tube 7 so as to provide in the region of the contacting surfaces 21 an adequate fluid-tightness preventing the egress of liquid 3, the portion 19 of tube 7 deforming and fitting closely around the contour of ball 9 which is non-deformable. The liquid 3 upstream of ball 9 is thus prevented from penetrating in non-controlled fashion into the downstream part 19 of the tube and unwantedly activating and setting off the detection means.

The means 11 for detecting displacement of the ball 9 comprise a chamber 23 in which are arranged two electrodes 25 and 27. The downstream end 19 of tube 7 leads into this chamber. Chamber 23 is enclosed in a sleeve 29 which is preferably cylindrical and whose upstream end 31 is tightly fitted on the derivation branch 17 and on the upstream part of tube 7 which is sandwiched between the sleeve 29 and branch 17. The downstream end 33 of sleeve is closed by the two electrodes 25 and 27. The internal diameter of sleeve 29 is greater than the external diameter of the portion 19 of tube 7, so as to leave an annular space j between these two elements wherein the tube 7 can deform radially during passage of the ball 9 therealong. Moreover, the sleeve 29 is longer than tube 7 so that the ball may completely move out of the latter. The sleeve 29 is preferably made of transparent plastic material, for example plexiglass or polycarbonate, to allow the ball 9 to be seen.

The first electrode 25 is in the form of a sleeve, preferably cylindrical, defining the downstream end of the walls of chamber 23. It is also possible for this electrode to extend along the entire length of the walls of chamber 23. The second electrode 27 is coaxial with and housed inside the first. This second electrode 27 is spaced apart from the first by an insulating ring 35, for example of "Delrin" or "Nylon" (Trademarks)

The first electrode 25 has an annular shoulder 37 and is force fitted in the sleeve 29 until this shoulder abuts against the end of this sleeve. The insulating ring 35 also has an annular shoulder 39 and is fitted in the same way in the first electrode 25. Lastly, the second electrode 27 is force fitted in the insulating ring 35. This second electrodes 27 has a cavity 41 leading into chamber 23, which cavity is defined by an annular wall 43. This second electrode 27 is spaced sufficiently away from the end of tube 7 to allow the ball 9 to move out into chamber 23.

The two electrodes are made of conductive metal, for example nickel-silver or nickel-bronze. These two electrodes 25 and 27 are each connected to a connection terminal 45 and 47 respectively. These terminals 45, 47 are connected in an electrical circuit (shown only in FIG. 7) able to generate an electrical signal when a displacement of the ball 9 has been detected This electrical signal may control either an alarm, or the immediate and definitive stopping of the pump's motor which, in normal operation, causes the liquid 3 to flow in the main pipe 1.

In the detector according to the invention, the obturator 9 (here a ball) moves between the initial position A it occupies during normal operation and a position B it occupies after a given over-pressure threshold in the pipe 1 has been exceeded. This over-pressure threshold is defined as a function of the diameter of ball 9 and the inner diameter of tube 7. The greater the diameter of ball 9 relative to the inner diameter of tube 7, the greater will be the magnitude of the over-pressure threshold before the ball 9 moves. This threshold is also a function of the elasticity of tube 7. In the initial position A, the ball 9 is located in the tube 7, adjacent the outlet of the derivation branch 17. In the final position B, it is outside tube 7 and located in the chamber 23. This detector is thus a single-use device because it is not possible to reintroduce the ball 9 in tube 7.

However, when starting up the entire device and particularly during the initial filling of pipe 1 with liquid 3, the pipe 1 may be subjected to an over-pressure exceeding the set threshold, to determine an anomalous operating condition that must be signalled during use. Clearly, in this case, this over-pressure must not cause ejection of the ball 9 from tube 7 during filling. For this purpose, there are provided means 49 for maintaining the ball 9 in its initial position A during the initial filling of pipe 1.

These maintaining means 49 comprise a piston 51 provided with a rod 52 and a head 53. Rod 52 is arranged coaxially in the second electrode 27 and is freely slidably mounted in a hole 54 in said electrode 57. Hole 54 leads into the cavity 41 in the middle of its shoulder-forming face 55. Moreover, rod 52 has an area of weakness 56 whereat it can be broken after it has been withdrawn following the filling operation. The result is shown in FIG. 1A. The diameter of head 53 is greater than the diameter of rod 52, which prevents the withdrawal of the inner part of the piston.

Lastly, there is provided in the sleeve 29 a vent 57 allowing evacuation of the air in chamber 23 and cavity 41 when ball 9 is expelled from tube 7. The outlet orifice of vent 57 is preferably provided with a liquid-absorbent patch 59 which prevents liquid 3 from leaving the detector when the ball 9 is in position B.

Operation of the described detector will now be explained in detail.

Figure 1B:
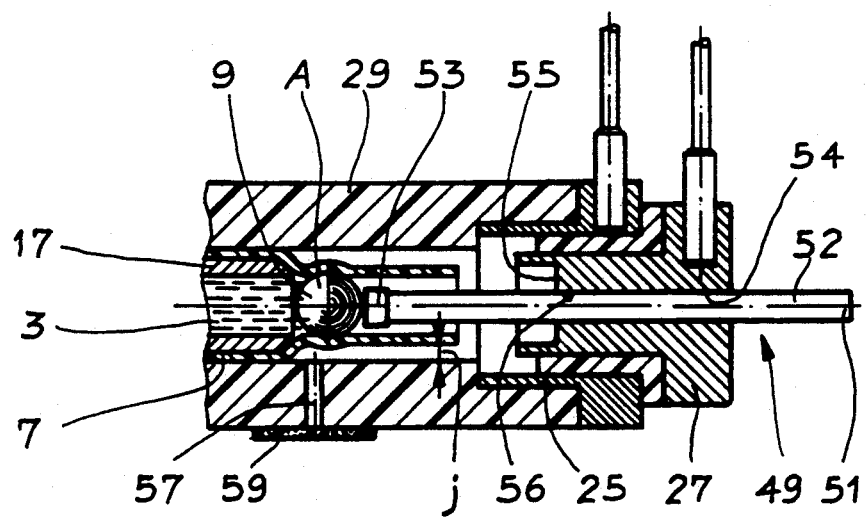
FIGS. 1B and 2B are partial cross-sectional views of the detector corresponding respectively to FIGS. 1A and 2A, but before operation of the detector, i.e. in the rest position.

FIG. 1B shows the initial position of piston 51 when the pipe 1 is initially filled. Piston 51 is arranged so that its head 53 contacts the ball 9 and maintains it in the initial position A, thus preventing any unwanted movement of the ball. When it is desired to actually use the detector, piston 51 is pulled out until its head 53 reaches the bottom of cavity 41 and abuts against face 55, whereupon the protruding end of piston 51 is broken at the predefined area of weakness 56. The detector is thus ready to operate (FIG. 1A).

When there is an over-pressure in the pipe 1, for instance if there is a blockage in the downstream part 1AV of this pipe, this over-pressure acts in the derivation branch 17. When the over-pressure exceeds a predetermined threshold, the ball 9 is driven out of tube 7 into chamber 23. The electrically conductive liquid 3 thus fills up this chamber and connects the electrodes 25 and 27, thereby closing the electrical circuit to which these electrodes are connected. An electrical signal is thus triggered, for example setting off an alarm. It is noted that the specific shape of the electrodes 25 and 27 and of cavity 41 provide a relatively large electrical contact surface for any given dimensions of the electrodes.

Figure 2A:
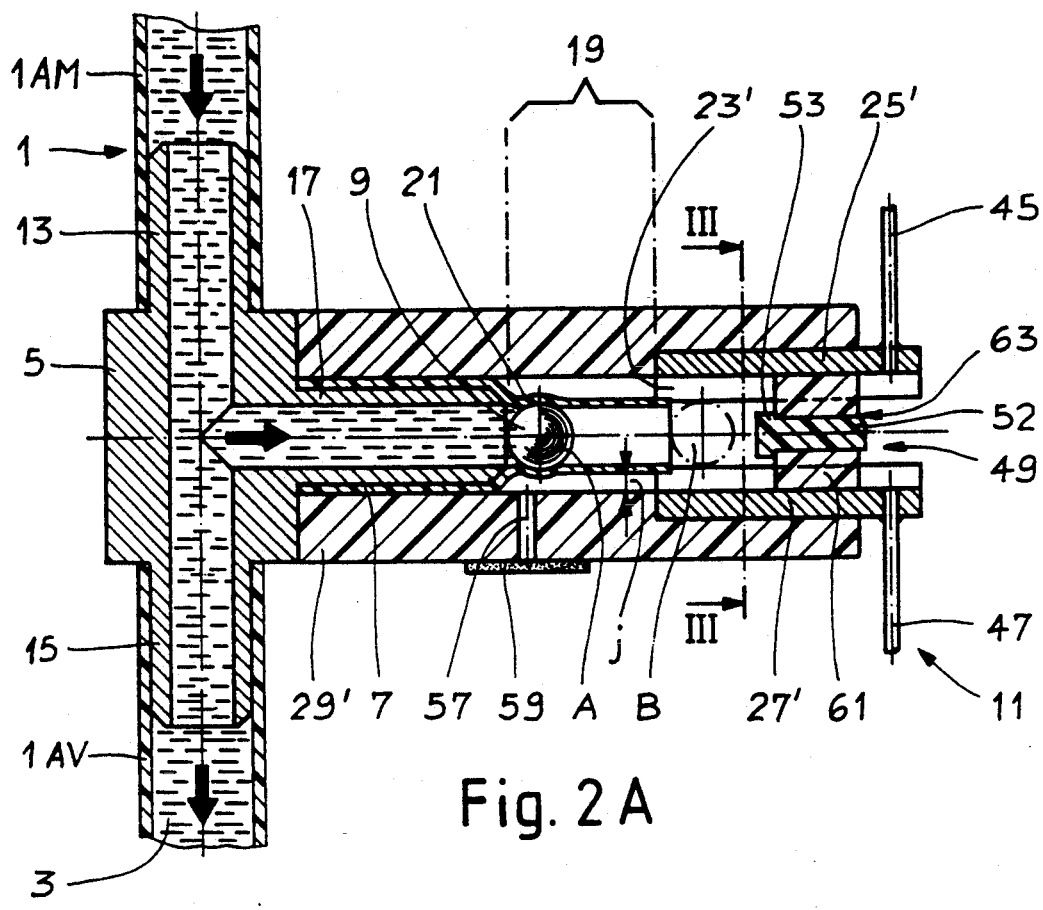

FIG. 2A shows a detector similar to that of FIG. 1A, but where the electrodes have a different shape.

The same elements of the two detectors are indicated by the same reference numbers. The two electrodes, indicated by references 25' and 27', are symmetrical, have the form of segments of a cylinder cut along its length (see FIG. 3), and are flush with the inner surface of the cylindrical sleeve indicated by reference 29'. These two electrodes 25' and 27' and sleeve 29' define a chamber 23'. In this embodiment, the two electrodes 25' and 27' are molded as inserts in the sleeve 29' of plastic material. The downstream end of sleeve 29' is closed by a wall 61 forming an electrically insulating closure member defining the bottom of chamber 23. The center of this wall 61 has a hole 63 receiving piston 51. Lastly, the two downstream ends of electrodes 25' and 27' extend beyond the sleeve 29' for the connection of connector terminals and 47.

Figures 2B, 3:
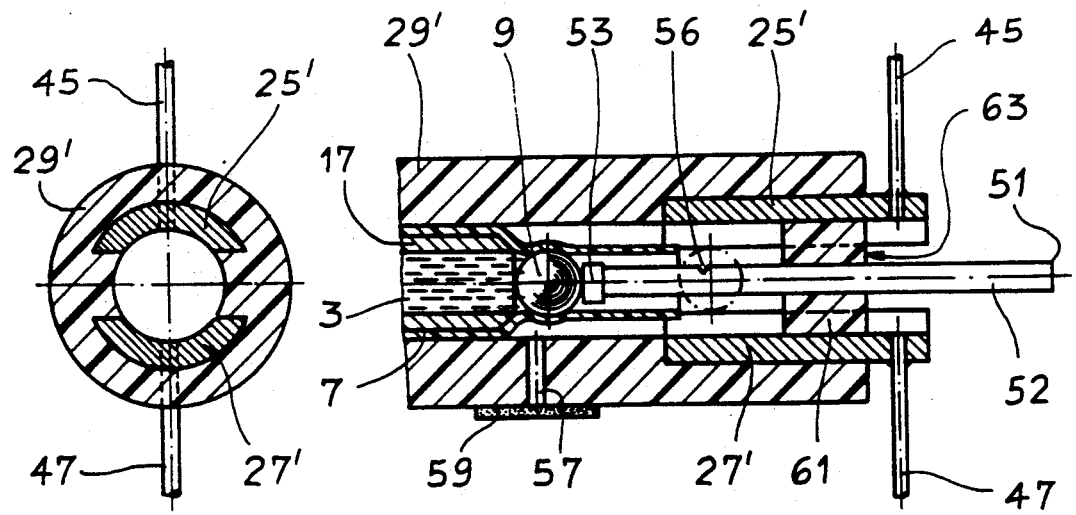
FIG. 3 is a cross-section along line III—III of FIG. 2A.

FIG. 2B, like FIG. 1B, illustrates the position of piston 51 when it bears against the ball 9 during the initial filling.

In a detector made by the Applicant, the following dimensions and values were used and are given here solely by way of example.

The tube 7, made for example of silicone polymer, had an inner diameter of 1.47 mm and an external diameter of 1.96 mm. The over-pressure required to eject the ball 9 from tube 7 was 0.4 to 0.5 bar (0.4 to $0.5 \times 10^5$Pa) for a ball diameter of 1.59 mm and 0.6 to 0.7 bar (0.6 to $0.7 \times 10^5$ Pa) for a ball diameter of 1.65 mm.

In an embodiment as shown, in FIGS. 1A, 1B the first electrode (the external electrode 25) had an active electrical contact surface area of 16.50 mm$^2$ and the internal electrode 27 an active surface area of 15.12 mm$^2$.

In an embodiment as shown in FIGS. 2A and 2B, the active contact surface area of each electrode 25' and 27' was 7.63 mm$^2$.

Figure 4:
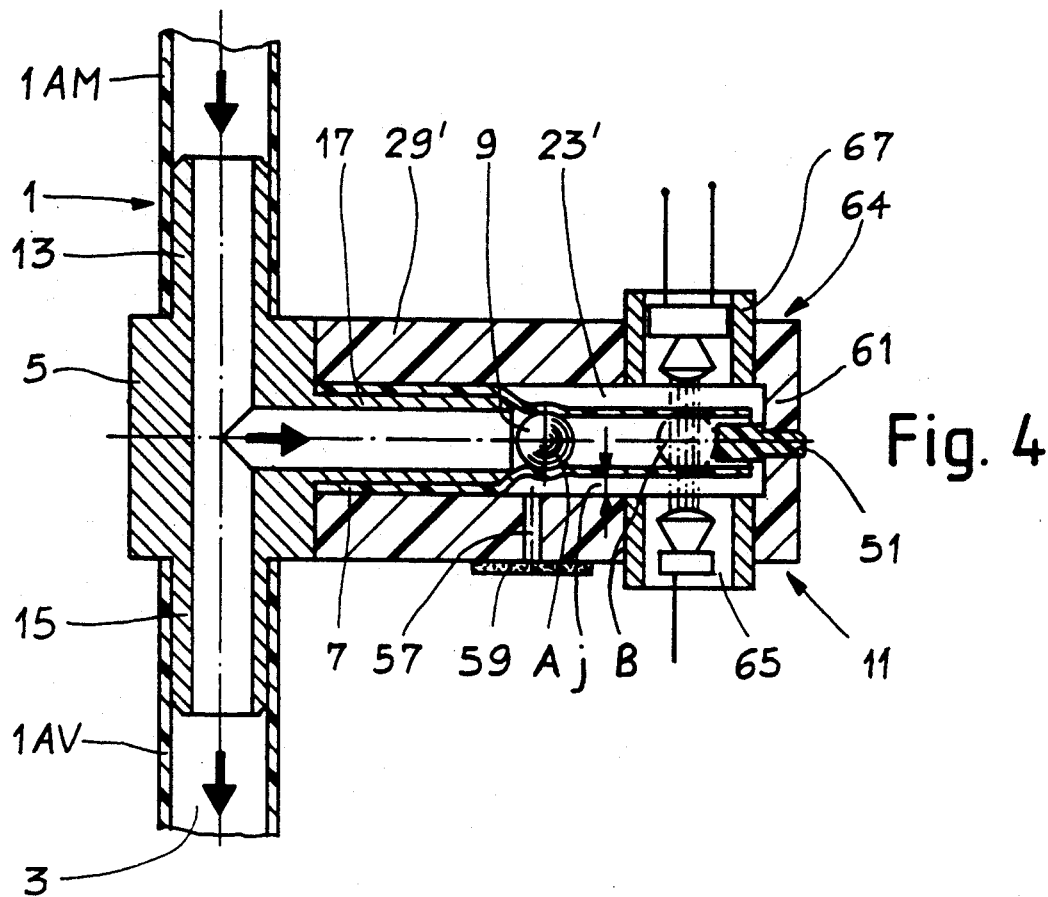
FIGS. 4, 5 and 6 are cross-sections respectively of third, fourth and fifth embodiments of the invention.

The third embodiment of the invention, shown in FIG. 4, will now be described. In this detector, only the means 11 for detecting the displacement of ball 9 are different. The other elements are the same as those of FIGS. 2A and 2B and are indicated by the same references.

In this embodiment, the flowing fluid 3 may be a non-conductive liquid or gas. Also, it is not necessary for the obturator, in this instance the ball 9, to have a contacting surface with an outer diameter greater than the inner diameter of the tube 7 to ensure perfect fluid-tightness. These two diameters can be the same. It is simply arranged that the ball 9 is held by friction in its initial position A. It is noted that the tube 7 extends substantially up to the rear wall 61 of sleeve 29'.

The means 11 for detecting displacement of the ball 9 comprise a photoelectric sensor 64 having a light source 65 and a receiver 67. Sensor 64 is arranged along the path of ball 9. More specifically, the emitter 65 and receiver 67 are arranged in the walls of the sleeve 29', on either side of the tube 7 and downstream of the ball 9.

Under the action of an over-pressure exerted by fluid 3, the ball 9 moves from its initial position A to its final position' B where it is placed between the light source 65 and receiver 67, thus actuating the sensor 64. The receiver may then emit an electric signal indicative of detection of the displacement of ball 9.

Figure 5:
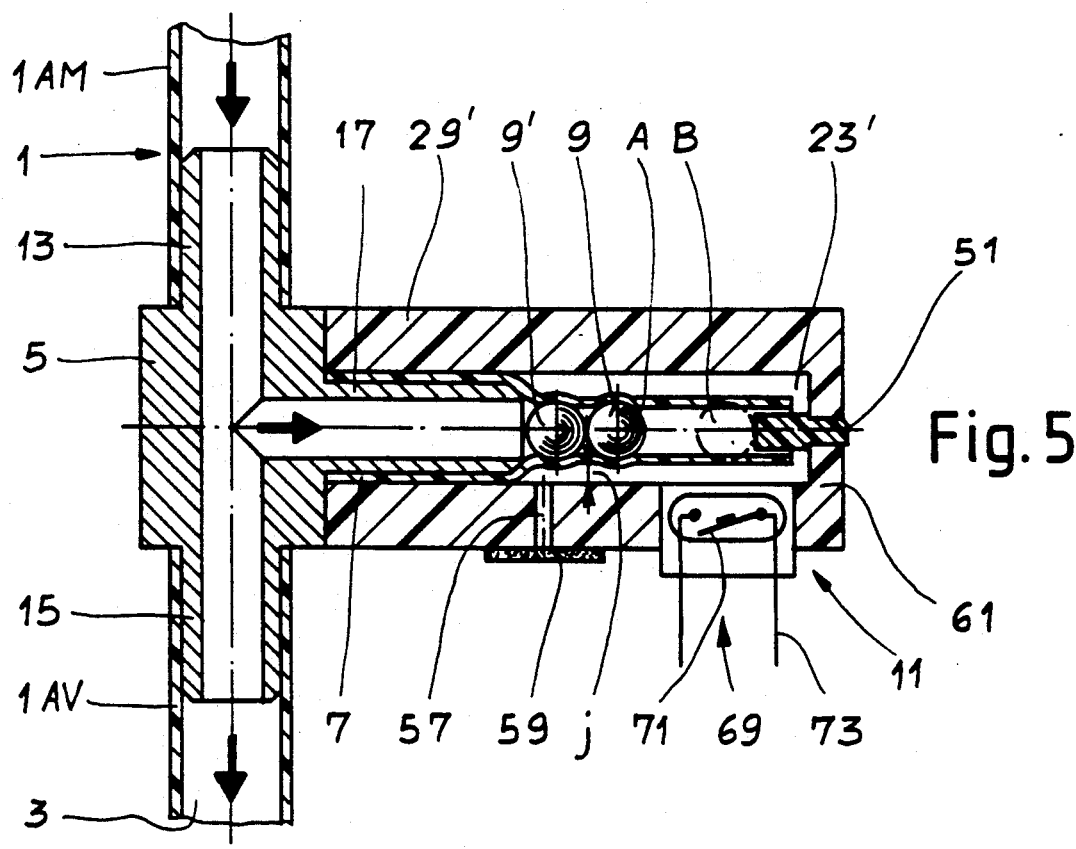
Figure 6:
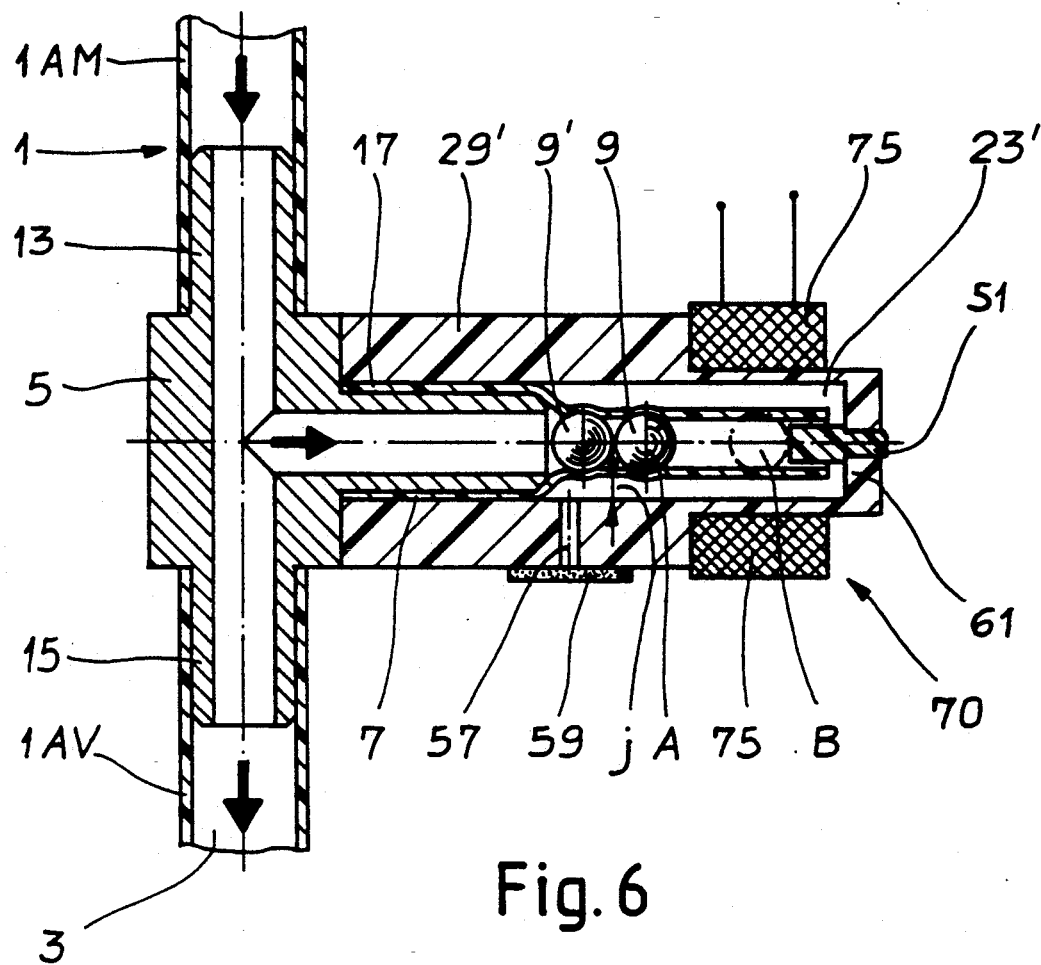

FIGS. 5 and 6 illustrate two further embodiments in which the photoelectric sensor 64 is replaced respectively by a magnetic sensor 69 and by an electromagnetic sensor 70. In both of these cases the fluid 3 may at choice be a liquid or a gas.

In FIG. 5, the magnetic sensor 69, arranged in sleeve 29', is a contact comprising an angularly mobile magnetized metal blade 71. Ball 9 is made of metal. When the ball 9 passes in front of blade 71, the latter trips and closes the electric circuit 73 thus setting off an electric signal.

It would also be possible to provide a non-magnetized metal blade 71 and a magnetized ball 9 or, preferably, a magnetized cylinder.

In FIG. 6, the electromagnetic sensor 70 is made up of a coil 75 arranged around the tube 7 and sleeve 29'.

In FIGS. 5 and 6, two balls 9 have been shown; the purpose of this will be explained in connection with FIG. 7.

Figure 7:
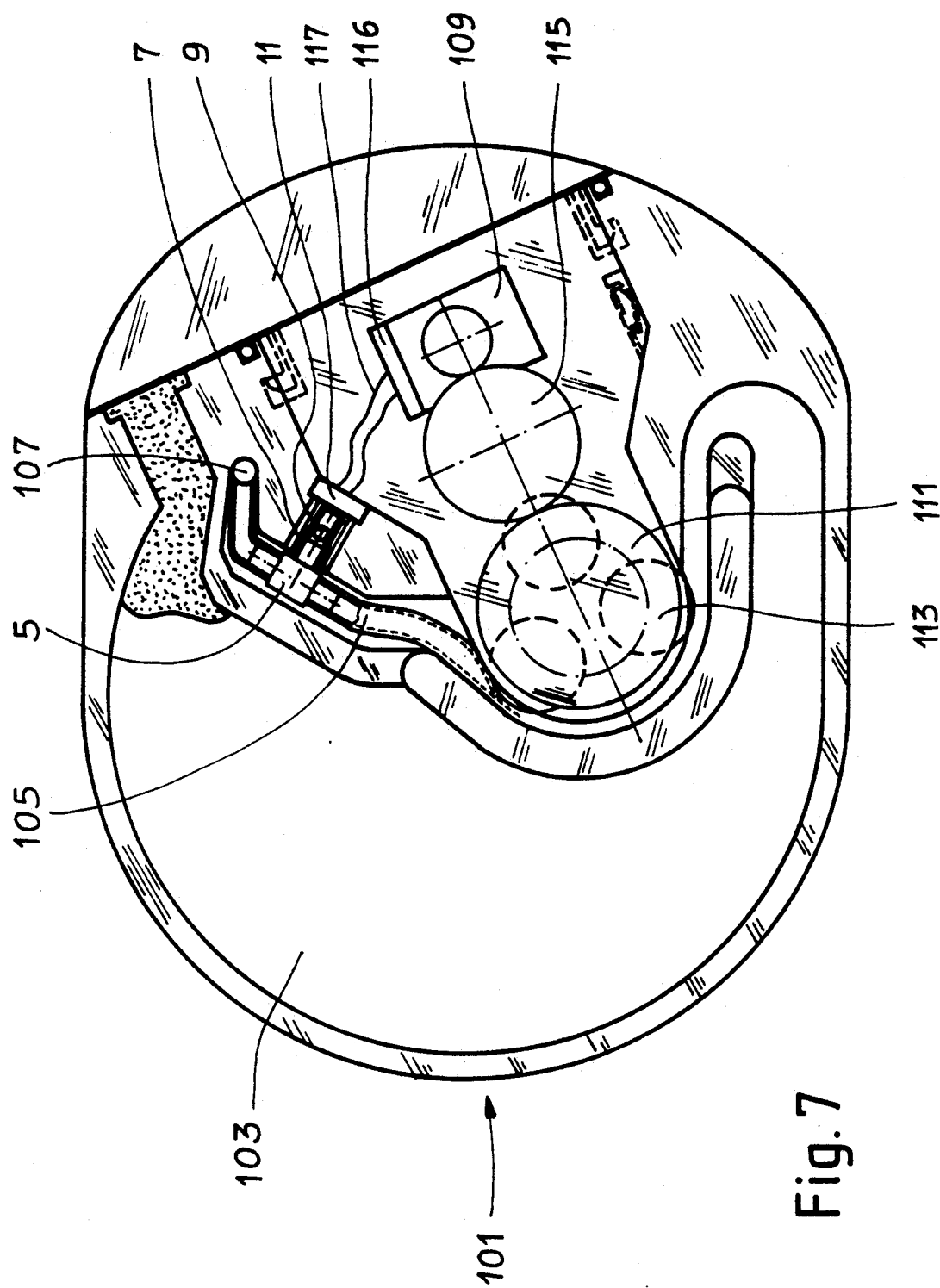
FIG. 7 is a cross-section of a medical pump including a detector according to the invention.

FIG. 7 illustrates a specific example of an application of the detector according to the invention. This FIG. shows a medical device, namely a peristaltic pump 101 for injecting into a patient a medicament which in this instance forms the circulating fluid 3.

This device 101 comprises a reservoir 103 for the medicament, connected by a supply pipe 105 to an outlet orifice 107 where a hypodermic needle (not shown) is fixed. A motor 109 drives a peristaltic pump 111 having pressure rollers 113, via a toothed wheel 115.

The detector according to the invention is placed between pump 111 and the outlet orifice 107. FIG. 7 shows the deriving means 5, tube 7, ball 9 and the means 11 for detecting displacement of the ball. The latter means are connected to motor 109 as well as to an alarm 116 by an electric circuit 117. If there is an over-pressure occurs in the supply pipe 105, the electric signal generated by the electric circuit 117 activates the alarm 116 and immediately stops the pump 111.

For medical applications, such as for this pump, the detector will be made of materials compatible with the medical use. Thus, the ball 9 will be made of a sterilizable medical material that is chemically neutral relative to the flowing fluid 3, for instance a plastic material such as PTFE (polytetrafluoroethylene), glass, ceramic or even possibly of a metal such as gold or platinum.

When the detectors of FIGS. 5 and 6 are used in this type of medical application, two balls 9 will be placed in the tube 7. The first or upstream ball 9' will be made of medical plastic material and the downstream ball 9 will of course be a magnetized or non-magnetized metal ball. Thus, the medicament will be in contact only with the upstream ball 9' made of sterilizable material and, when the two balls 9, 9' have been driven out by over-pressure, the metal ball 9 will set off the magnetic or electromagnetic sensors.

The previously-indicated numerical values given by way of example apply in particular to a medical pump of small dimensions. However, the dimensions of the detector could be increased for other applications.

In all of the previously described embodiments, the obturator(s) 9 (9') is (are) made of non-deformable material while tube 7 is made of resilient material able to slightly elastically deform around the obturator(s) thereby providing for not only holding the obturator in its initial position A but, also, fluid-tightness. The same result could however be achieved by making the tube 7 of non-deformable material and the obturator 9, 9' of an elastically expansible material that is deformed inside the tube.

Lastly, it would be possible to connect several detectors in parallel to the same pipe 1, these detectors having different ratios between the diameter of the ball 9 and the inner diameter of tube 7, or having tubes 7 of different elasticities. These detectors would be responsive to different thresholds of over-pressure. Thus, a first detector could set off an alarm when there is a small over-pressure, and a second could stop the pump motor when there is a strong over-pressure.

I claim:

1. A detector for detecting over-pressure in a pipe in which a fluid flows, this detector being adapted to produce a signal when an over-pressure threshold is reached and comprising:
   means for deriving a fraction of said fluid from the pipe;
   at least one tube wherein there is fitted at least one obturating member, said tube being connected at its upstream end to said deriving means, an element of at least one of said tube and said obturating member being resiliently deformable to retain said obturating member in said tube in a normal operating position by means of frictional forces generated at their contacting surfaces, and the obturating member leaving the normal operating position when the pipe is subjected to an over-pressure sufficient to overcome the frictional forces; and,
   means for detecting the displacement of said obturating member and for generating said signal in response to detecting displacement of the obturating member.

2. A detector according to claim 1, wherein said tube is made of an elastic material and said obturating member is a non-deformable body friction fitted in said tube.

3. A detector according to claim 1, wherein the diameter of the obturating member at the contact surface with the tube is greater than the inner diameter of the tube to prevent fluid in the upstream part of the tube from penetrating into its downstream part.

4. A detector according to claim 1, wherein the obturating member is a ball.

5. A detector according to claim 1, wherein the deriving means comprise a T junction having two branches adapted to be connected in the pipe and a third branch connected to the upstream end of said tube.

6. A detector according to claim 1 for over-pressure in a pipe in which an electrically conductive liquid flows, wherein the means for detecting the displacement of the obturating member comprises a chamber in which at least two electrodes are spaced apart from one another, the downstream end of said tube leading into this chamber and the electrodes being connected to an electric circuit able to generating said signal.

7. A detector according to claim 6, wherein a first electrode is in the form of a sleeve defining at least a part of the walls of said chamber and a second electrode (27) is housed inside the first electrode and has a cavity leading into the chamber, said cavity being defined by an annular wall.

8. A detector according to claim 6, wherein each electrode has the shape of a segment of a cylinder cut lengthwise and arranged in the wall of the chamber.

9. A detector according to claim 6, wherein the chamber has venting means.

10. A detector according to claim 1, wherein said means for detecting displacement of the obturating member comprises a photoelectric sensor arranged along the path of said obturating member to be actuated by displacement thereof.

11. A detector according to claim 1, wherein the obturating member is made of a sterilizable medical material that is chemically neutral to the flowing fluid.

12. A detector according to claim 1, wherein the obturating member is made of metal.

13. A detector according to claim 1, wherein the obturating member is made of a plastic material such as polytetrafluoroethylene, a ceramic material or a glass.

14. A detector according to claim 1, wherein the means for detecting displacement of the obturating member comprises a magnetic or an electro-magnetic sensor arranged along the path of the obturating, member so as to be actuated upon displacement of the obturating member.

15. A detector according to claim 14, wherein two obturating members are placed in the tube, a first obturating member made of sterilizable medical material being arranged in the upstream part of the tube and a second obturating member made of metal being arranged in the downstream part of the tube.

16. A detector according to claim 1, wherein the signal generated by the means for detecting displacement of the obturating member is supplied to means for setting off an alarm.

17. A detector according to claim 1, comprising means for maintaining the obturating member in its position for normal operation, this maintaining means being withdrawable to place the detector in its operative condition.

18. A detector according to claim 17, wherein the means for maintaining the obturating member comprise a piston arranged coaxially in the tube.

19. A pump driven by a motor, comprising a detector according to claim 1 arranged in a supply pipe of this pump, and means for causing the signal generated by the means for detecting displacement of the obturating member to control immediate stopping of said motor.

20. A pump according to claim 19, which is a medical pump and wherein the fluid is a medication.

* * * * *

UNITED STATES PATENT AND TRADEMARK OFFICE
CERTIFICATE OF CORRECTION

PATENT NO. : 5,235,324
DATED : August 10, 1993
INVENTOR(S) : Eric GAGNEBIN

It is certified that error appears in the above-identified patent and that said Letters Patent is hereby corrected as shown below:

Column 8, line 6, delete "(27)" and line 30, after "obturating" delete ",".

Signed and Sealed this

Fifteenth Day of March, 1994

BRUCE LEHMAN

Attest:

Attesting Officer

Commissioner of Patents and Trademarks